United States Patent [19]
Pohndorf

[11] Patent Number: 5,273,053
[45] Date of Patent: Dec. 28, 1993

[54] SUTURE SLEEVE WITH LEAD LOCKING DEVICE

[75] Inventor: Peter J. Pohndorf, Stillwater, Minn.

[73] Assignee: Medtronic, Inc., Minneapolis, Minn.

[21] Appl. No.: 971,017

[22] Filed: Nov. 2, 1992

[51] Int. Cl.⁵ .............................................. A61N 1/05
[52] U.S. Cl. .................................... 607/132; 604/175
[58] Field of Search ............................... 128/783-786, 128/639, 642, 419 P; 604/171, 174-175, 178, 180

[56] References Cited

U.S. PATENT DOCUMENTS

| | | | |
|---|---|---|---|
| 3,176,690 | 4/1965 | H'Doubler | 128/348 |
| 4,276,882 | 7/1981 | Dickhudt et al. | 128/419 P |
| 4,287,891 | 9/1981 | Peters | 128/34 |
| 4,516,584 | 5/1985 | Garcia | 128/785 |
| 4,553,961 | 11/1985 | Pohndorf et al. | 604/175 |
| 4,672,979 | 6/1987 | Pohndorf | 128/784 |
| 4,860,750 | 8/1989 | Frey et al. | 128/419 P |
| 5,107,856 | 4/1992 | Kristiansen et al. | 128/785 |
| 5,129,405 | 7/1992 | Milijasevic et al. | 128/785 |
| 5,152,298 | 10/1992 | Kreyenhagen et al. | 128/784 |

FOREIGN PATENT DOCUMENTS 2662310 5/1991 France .

Primary Examiner—Kyle L. Howell
Assistant Examiner—Angela D. Sykes
Attorney, Agent, or Firm—Reed A. Duthler; Harold R. Patton

[57] ABSTRACT

A suture sleeve for facilitating the ligature of an implanted lead to a patient's vein or underlying tissue. The suture sleeve comprises a main sleeve body having a first, longitudinal throughbore for receiving the lead. The suture sleeve is provided with a manually-actuated pushbutton-type locking mechanism. With the locking mechanism in an unlocked condition, the suture sleeve is allowed to freely move back and forth along the lead body. When the locking mechanism is actuated with a simple pushbutton action, the suture sleeve is substantially prevented from sliding along the lead body. The pushbutton mechanism is adapted to be movably received in a second throughbore in said sleeve body, the second throughbore being substantially perpendicular to the first longitudinal throughbore. The pushbutton mechanism has a throughbore of substantially the same diameter as the first longitudinal throughbore in the sleeve body. When the pushbutton mechanism is in the unlocked position, the pushbutton throughbore is in substantial coaxial alignment with the longitudinal throughbore in the sleeve body. When the pushbutton mechanism is in the locked position, the pushbutton throughbore is offset from the longitudinal sleeve body throughbore, thereby exerting pressure against the side of the lead body and securing the suture sleeve in place on the lead body.

8 Claims, 10 Drawing Sheets

SUTURE SLEEVE WITH LEAD LOCKING DEVICE

FIELD OF THE INVENTION

This invention relates to the field of implantable medical devices, and more particularly relates to suture sleeves for implantable leads, catheters, and the like.

BACKGROUND OF THE INVENTION

Implantable leads are used in conjunction with many different types of therapeutic medical devices, such as pacemakers, cardioverters, cardiac defibrillators, neural stimulators, and the like. It is generally deemed desirable to secure an implantable lead in some manner so that proper positioning and placement of the lead is not disturbed. In the past, various techniques and mechanisms have been proposed for securing implanted or partially implanted leads in a patient. When transvenous leads were first introduced in the 1970's, physicians often employed a "butterfly-type" anchoring sleeve provided with the lead. The anchoring sleeve, attached to the lead body during implantation, provided a structure adapted to be sutured to a vein or underlying tissue, and further protected the lead insulation from the stress of having a suture tied around it.

When polyurethane leads were introduced in the late 1970's, they were frequently provided with a prefitted sleeve to facilitate the securing the lead with sutures. Such sleeves were particularly advantageous for polyurethane leads, which tended to have thinner insulation layers than earlier leads. The sleeves were typically silicone rubber, and adapted to slide along the lead body. In operation, the physician would slide the sleeve to a position near where the lead enters the vein, and suture the sleeve to the vein or to underlying tissue to secure the lead.

Several examples of prior art suture sleeves are known in the prior art, including those disclosed in U.S. Pat. No. 4,516,584 issued on May 14, 1985 to Garcia entitled "Suture Collar" (cylindrical collar with longitudinal bore); U.S. Pat. No. 4,553,961 issued on Nov. 19, 1985 to Pohndorf et al. entitled "Suture Sleeve with Structure for Enhancing Pacing Lead Gripping" (cylindrical collar with longitudinal bore containing structure for enhancing gripping between collar and lead); U.S. Pat. No. 4,672,979 issued on Jun. 16, 1987 to Pohndorf entitled "Suture Sleeve Assembly" (tubular sleeve and collet member adapted to snap together); U.S. Pat. No. 4,683,895 issued on Aug. 4, 1987 to Pohndorf entitled "Suture Sleeve Anchoring Device" (circular staple-like clip for attaching a suture sleeve to tissue); U.S. Pat. No. 5,107,856 issued on Apr. 28, 1992 to Kristiansen et al. entitled "Multiple Lead Suture Sleeve" (generally "W"-shaped sleeve adapted to be compressed by sutures around one or two leads); and U.S. Pat. No. 5,129,405 issued to Milijasevic et al. on Jul. 14, 1992 entitled "Vein Suture Collar" (cylindrical collar with longitudinal bore).

Other tubular member securing mechanisms have been proposed in the prior art. Earlier examples include U.S. Pat. No. 3,176,690 issued on Apr. 6, 1965 to H'Doubler entitled "Catheter Having Integral, Polymeric Flanges" (elongated external flange integrally formed in the catheter body); U.S. Pat. No. 3,730,187 issued on May 1, 1973 to Reynolds (securing collar permanently located on the outer surface of the catheter and having a dacron suture embedded therein); and U.S. Pat. No. 3,724,467 issued on Apr. 3, 1973 to Avery et al. entitled "Electrode Implant for the Neuro-Stimulation of the Spinal Cord" (physiologically inert plastic tiedown clamp); which described various types of collars or tabs attached to the tubular member for providing a suturing structure.

Still other types of lead or catheter securing devices are disclosed, for example, in U.S. Pat. No. 3,821,957 issued on Jul. 2, 1974 to Riley et al. entitled "Retention Slide for Catheters and Other Tubular Materials" (retention slide having tubular portion and four flexible, radially projecting tabs); U.S. Pat. No. 3,880,169 to Starr et al. on Apr. 29, 1975 entitled "Controlled Entry Pacemaker Electrode for Myocardial Implantation" (rectangular sewing pad adhesively bonded near distal end of lead and providing wings for suturing); U.S. Pat. No. 4,266,552 issued to Dutcher et al. on May 12, 1981 to Dutcher et al. entitled "Lead Anchoring Bobbin" (silicone rubber bobbin for receiving a looped portion of the lead); U.S. Pat. No. 4,276,882 issued on Jul. 7, 1981 to Dickhaudt et al. entitled "Lead Anchoring Device" (two-piece disc-shaped device for clamping one or more leads therebetween); and U.S. Pat. No. 4,287,891 issued on Sep. 8, 1981 to Peters entitled "Securing Device" (two-piece cylindrical device with longitudinal bore which grips tubular member when twisted).

The present inventor believes that known silicone rubber suture sleeves have several disadvantages. Sleeves which must be placed on the lead during manufacture can only be removed by cutting them off, as with a scalper, when physicians do not wish to use them. This is considered undesirable, since there is a risk that the insulation of the lead would be damaged while the sleeve was being cut off.

Moreover, it has been the inventor's experience that when a silicone rubber suture sleeve becomes wet or infiltrated by moisture, the friction between the lumen of the sleeve and the lead may be reduced so much that the lead is allowed to slide, and is no longer anchored in place.

SUMMARY OF THE INVENTION

In accordance with the present invention, a suture sleeve is provided which has a manually actuated locking mechanism therein for securing the sleeve at any desired position along the lead body. The sleeve is fitted onto the lead body during manufacture and, with the locking mechanism in an unlocked position, is allowed to freely slide along the length of the lead body. While the lead is being implanted into a patient, the physician can move the sleeve along the lead body to any desired position. Then, the physician actuates the simple pushbutton-type locking mechanism, causing the sleeve to be tightly secured to the lead body at the desired position. The sleeve has conventional circumferential grooves therearound, for facilitating the suturing the sleeve and lead to a vein or underlying tissue in the patent in the usual and well-known manner. The locking mechanism is designed to hold the lead body securely when it is in a locked position, but yet not exert so much pressure on the lead body as to cause damage to the lead. The sleeve disclosed herein is small and simple to use, and is believed to be more reliable than previous lead securing devices.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF A SPECIFIC EMBODIMENT OF THE INVENTION

Figure 1:
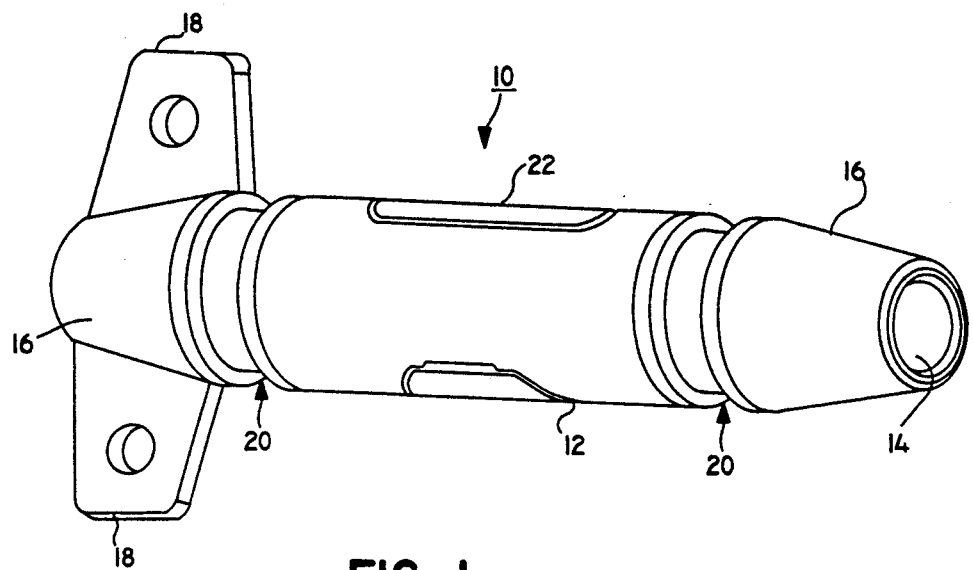
FIG. 1 is a perspective view of a suture sleeve in accordance with one embodiment of the present invention.

Referring to FIG. 1, there is shown a perspective view of a suture sleeve 10 in accordance with one embodiment of the present invention. It is to be understood that while suture sleeve 10 is shown in isolation in FIG. 1 (i.e., no lead is shown), it is contemplated that the present invention may advantageously be practiced by having sleeve 10 fitted onto an implantable lead during the manufacturing process. This is so mainly because leads are typically provided with connectors, electrodes, or other permanent structures at their proximal and distal ends, making it impossible to fit sleeve 10 onto the leads after manufacture.

As shown in FIG. 1, suture sleeve 10 comprises a main cylindrical body 12 having a longitudinal cylindrical bore 14 therethrough. Cylindrical body 12 of sleeve 10 is, in the presently preferred embodiment of the invention, made of hard, injection-molded plastic. Attached to each end of rigid cylindrical body 12 are less rigid, tapered endpieces 16. Endpieces 16, in the presently preferred embodiment of the invention, are made of silicone rubber or another suitably biocompatible, resilient material. Endpieces 16 are intended to serve as strain relief collars for preventing sharp and excessive bending of the lead in the region of the suture sleeve, which could lead to damage to the lead and possible fatigue-related failure of internal lead structures.

With continued reference to FIG. 1, one of the endpieces 16 may optionally be provided with radially-projecting fins or tabs 18 for providing a suturing structure in a manner similar to that shown in prior art, for example, in the aforementioned U.S. Pat. Nos. 3,176,600 to H'Doubler and 5,107,856 to Kristiansen et al. However, it is believed by the inventor that tabs 18 shown in FIG. 1 are not essential to practicing the present invention. In fact, the inventor has contemplated providing a weakened area near the points of attachment of tabs 18 to endpiece 16, so that tabs 18 might be easily removed (i.e., torn, pulled, or cut off) should the implanting physician choose not to utilize suture tabs 18.

Each endpiece 16 has at least one circumferential groove 20 on its outer surface, for allowing sleeve 10 to be sutured to a vein or underlying tissue in a conventional manner similar to that described, for example, in the aforementioned U.S. Pat. Nos. 4,516,584 to Garcia, 4,533,961 to Pohndorf et al., 4,672,979 to Pohndorf, or 5,129,405 to Milijasevic et al.

Finally, sleeve 10 is provided, in its main cylindrical body 12, with a pushbutton-type locking mechanism 22 (only partially visible in FIG. 1) to be described in greater detail below with reference to later Figures.

Figure 2:
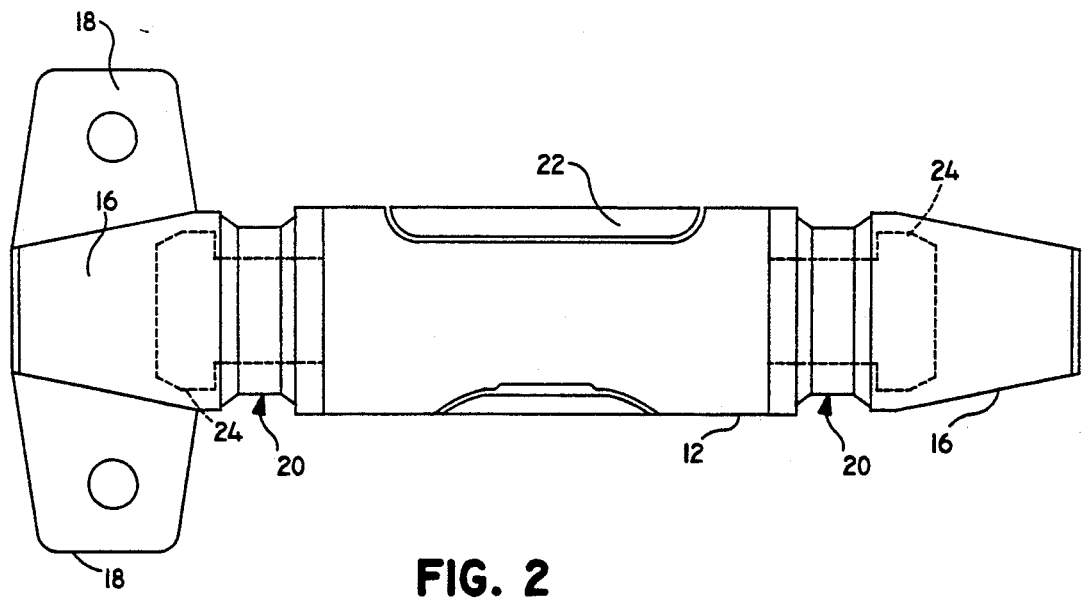
FIG. 2 is a side view of the suture sleeve from FIG. 1.

A side view of sleeve 10, showing main body 12, endpieces 16, optional tabs 18, grooves 20, and part of locking mechanism 22, is provided in FIG. 2. FIG. 2 also shows how silicone rubber endpieces 16 are attached to the respective ends of cylindrical body 12. In particular, cylindrical body 12 is provided with substantially cylindrical end portions, indicated by dashed lines 24 in FIG. 2, which are flared at their respective extreme ends to provide a structure to be engaged by molded silicone rubber end pieces 16. It should be noted with reference to FIG. 2 that grooves 20 in endpieces 16, when endpieces 16 are fitted onto the respective ends of body 12, are each disposed around a portion of a respective flared end portion 24. This is a notable feature of the present invention, since the rigidity of body 12, and in particular, the rigidity of end portions 24 of body 12, prevents sutures tied around grooves 20 from being pulled so tight as to cause ligature damage to the lead. The sutures in grooves 20 function to attach sleeve 10 to a vein or underlying tissue in the patient, but preferably do not function to secure sleeve 10 to the lead. Securing sleeve 10 to a lead is instead accomplished by means of locking mechanism 22, as will become hereinafter apparent.

Figure 3A:
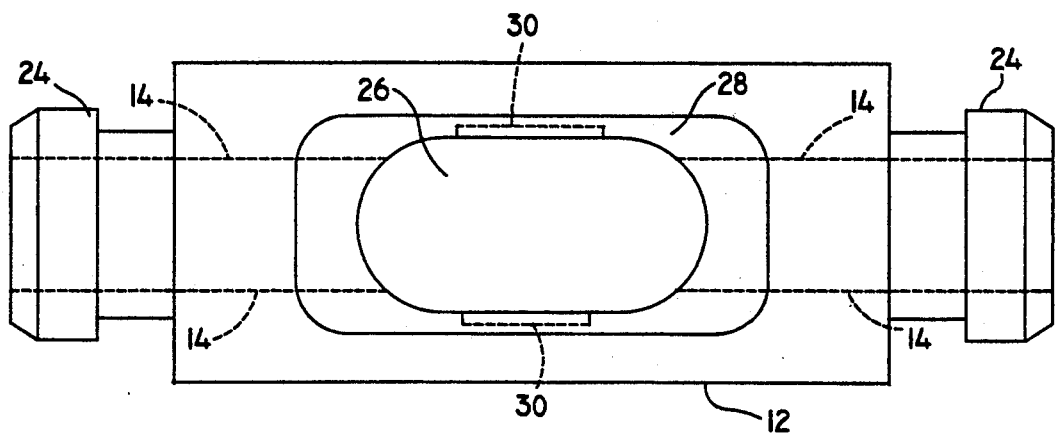
FIGS. 3a, 3b, and 3c are top, side, and bottom views, respectively, of the sleeve body from the suture sleeve of FIG. 1.
Figure 3B:
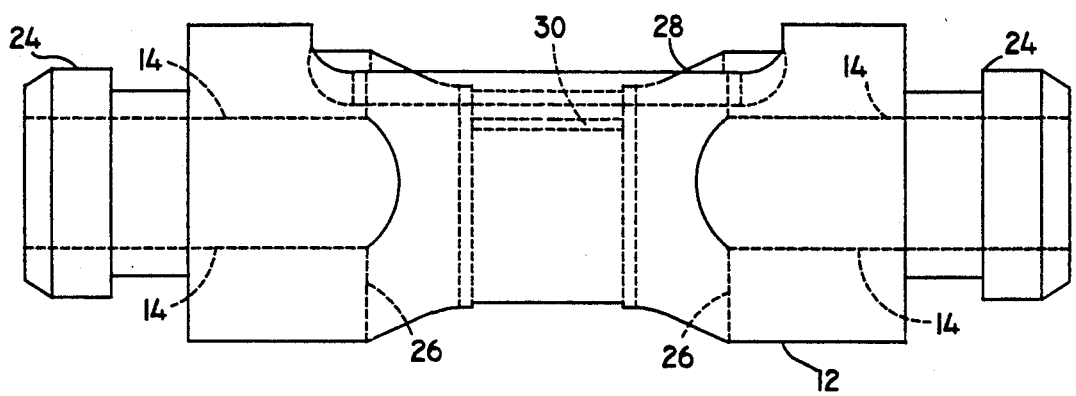
Figure 3C:
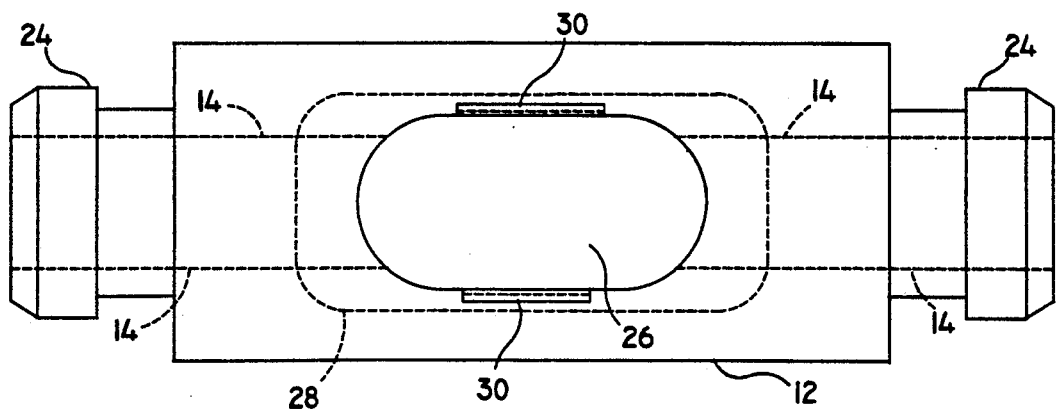

Turning now to FIGS. 3a, 3b, and 3c, there are shown top, side, and bottom views, respectively, of cylindrical body 12 from FIGS. 1 and 2. Note in FIGS. 3a, 3b, and 3c that end pieces 16 are not shown.

In FIGS. 3a, 3b, and 3c, dashed lines indicate the extent of cylindrical bore 14 which runs through the length of body 12. Referring first to the top view of FIG. 3a, body 12 has an oblong bore or channel 26, perpendicular to and intersecting cylindrical bore 14, extending from the top to the bottom of body 12. Additionally, channel 26 is disposed within a shallow recess 28 formed in the top of body 12. Shallow recess 28 is also visible in FIG. 3b, wherein oblong channel 26 is designated by dashed lines. In the bottom view of FIG. 3c, shallow recess 28 is indicated by a dashed line.

With reference to FIGS. 3a, 3b, and 3c, oblong channel 26 has two elongated, shallow indentations 30, one disposed on each of two of its sides, running generally parallel to cylindrical bore 14.

Turning now to FIGS. 4a, 4b, 4c, and 4d, there are shown top, side, bottom, and end views, respectively, of pushbutton locking mechanism 22 partially shown in FIGS. 1 and 2. Pushbutton locking mechanism 22 (hereinafter referred to as pushbutton 22 for convenience) is adapted to be received within oblong channel 26 in sleeve body 12, as will be shown in later figures.

Referring to FIGS. 4a, 4b, 4c, and 4d, pushbutton 22 comprises a main plunger body 32 and a top 34. As revealed in the side view of FIG. 4b and the end view of FIG. 4d, pushbutton top 34 is curved so that when pushbutton 22 is fully inserted into oblong channel 26 of sleeve body 12 (as will be hereinafter described in greater detail), pushbutton top 22 is received within shallow recess 28 in sleeve body 12 with the top of pushbutton top 22 flush with and matching the outer curvature of sleeve body 12. This is shown in FIGS. 1 and 2. In addition, as is also revealed in the side view of FIG. 4b and the end view of FIG. 4d, the bottom of pushbutton plunger 32 is also curved so that when pushbutton 22 is fully inserted into oblong channel 26 in sleeve body 12, the bottom of pushbutton plunger 32 is flush with and matching the outer curvature of sleeve body 12.

Figure 4A:
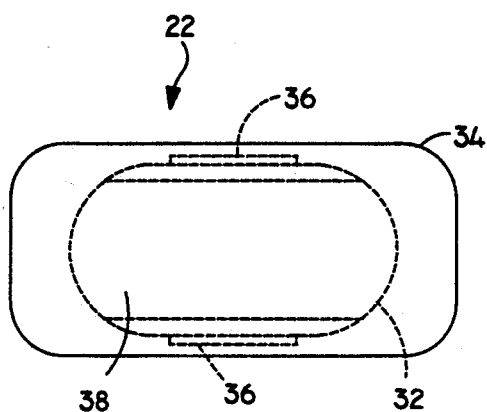
FIGS. 4a, 4b, 4c, and 4d are top, side, bottom, and end views, respectively of the pushbutton mechanism in the suture sleeve of FIG. 1.
Figure 4B:
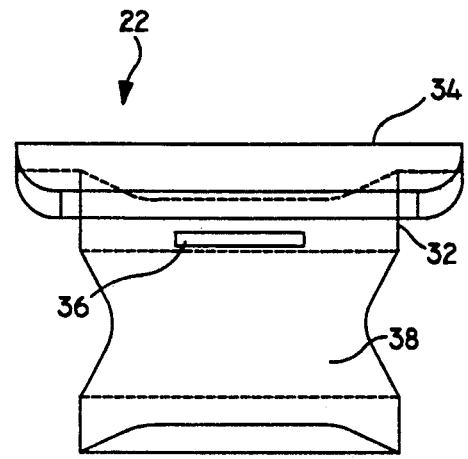
Figure 4C:
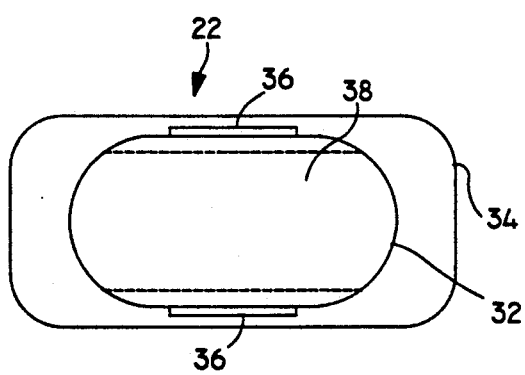
Figure 4D:
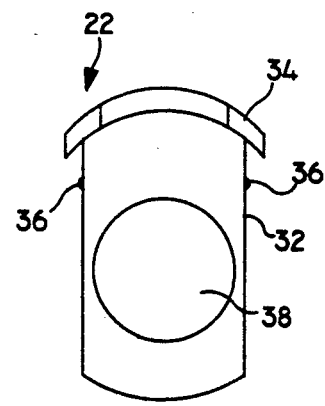

Referring to FIGS. 4b and 4d, plunger 32 has a narrow, longitudinal protrusion or detent 36 disposed on each of two of its sides. Detents 36 are adapted to be received in corresponding longitudinal grooves 30 disposed on the side walls of oblong channel 26 previously described with reference to FIGS. 3a, 3b, and 3c.

Figure 5A:
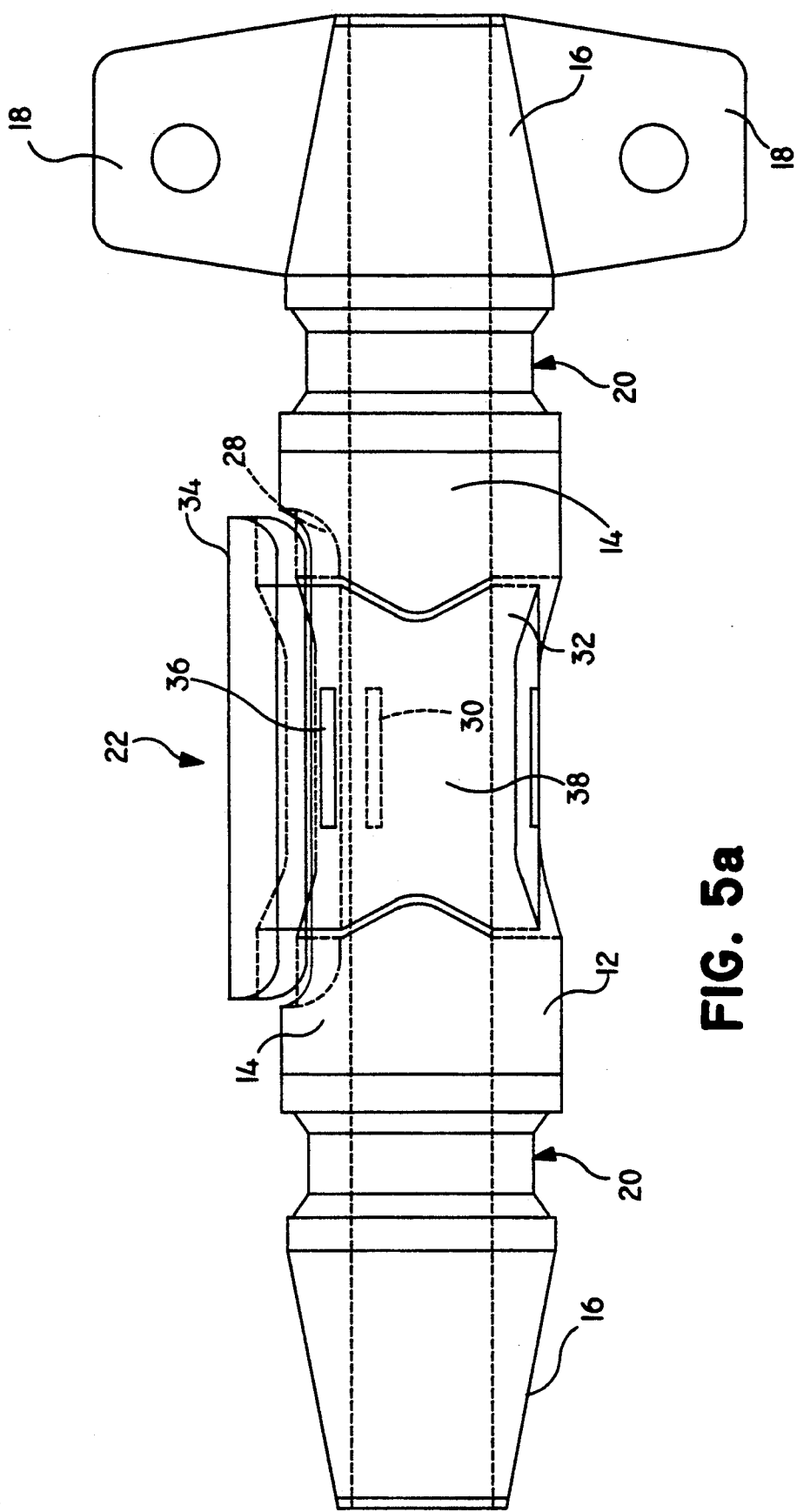
FIGS. 5a and 5b are side views of the sleeve of FIG. 1 showing the pushbutton locking mechanism in unlocked and locked positions, respectively.

A longitudinal cylindrical bore 38 is provided in pushbutton plunger body 32. Cylindrical bore 38 in plunger 32 has substantially the same diameter as cylindrical bore 14 in sleeve body 12, so that in one position where plunger 32 has not been fully inserted into oblong channel 26 in sleeve body 12, cylindrical bores 14 and 38 in sleeve body 12 and plunger 32, respectively, are in substantial coaxial alignment. That is, with pushbutton 22 in one partially inserted position in sleeve body 12, a single cylindrical bore is defined throughout the entire sleeve/pushbutton combination. This alignment of cylindrical bores 14 and 38 is depicted in FIG. 5a.

Figure 5B:
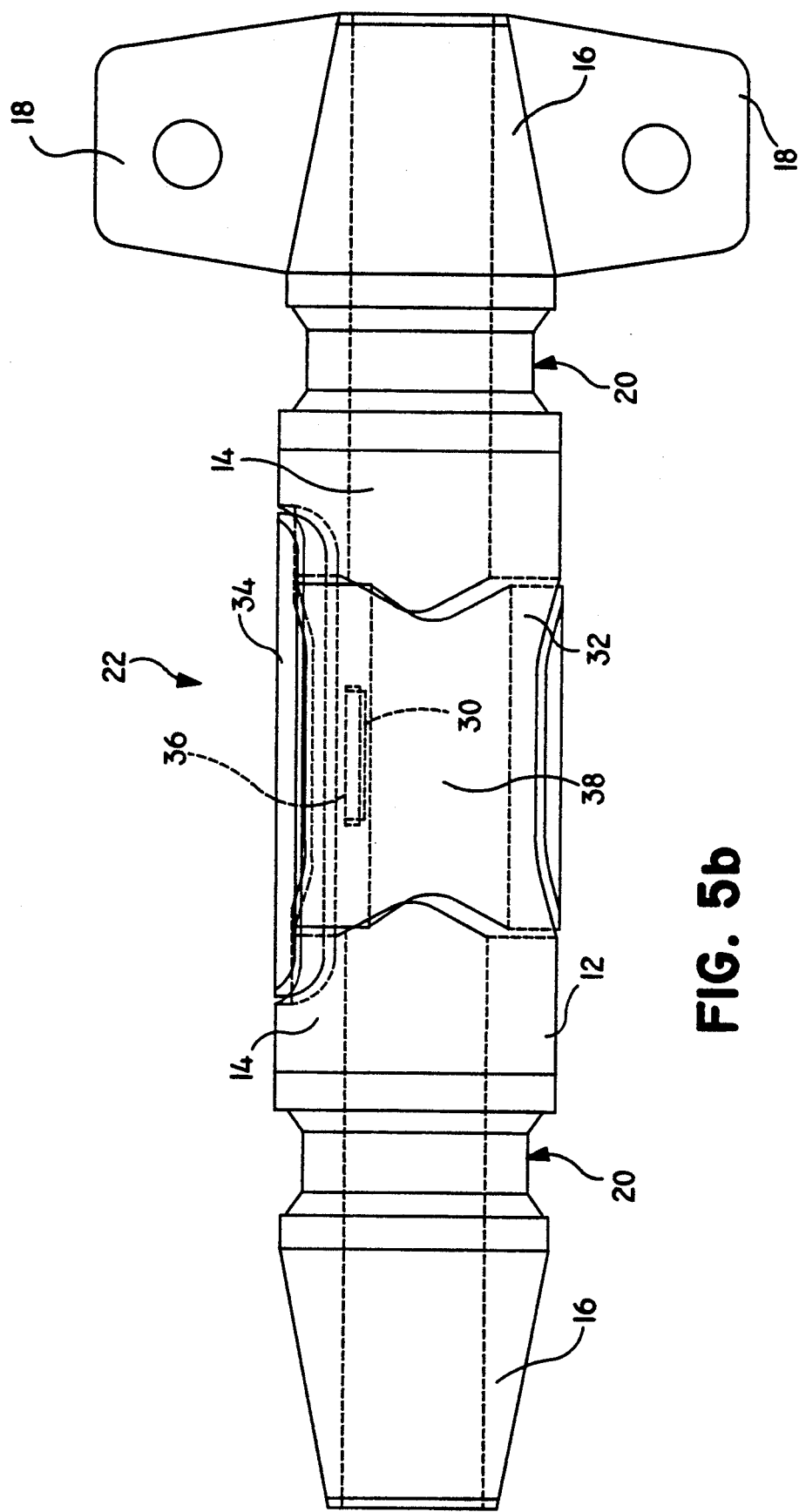

In a second position, however, when pushbutton top 34 is fully depressed into recess 28, so that the upper surface of pushbutton top 34 is substantially flush with the outer cylindrical surface of sleeve body 12, cylindrical bore in plunger 32 is no longer in substantial coaxial alignment with cylindrical bore 14 in sleeve body 12. Instead, when pushbutton top 34 is fully depressed into recess 28, with the upper surface of pushbutton top 34 being substantially flush with the outer cylindrical surface of sleeve body 12 as depicted in FIG. 5b, the axis of cylindrical bore 38 is slightly offset (in FIG. 5b, lower) from the axis of cylindrical bore 38.

Figure 6A:
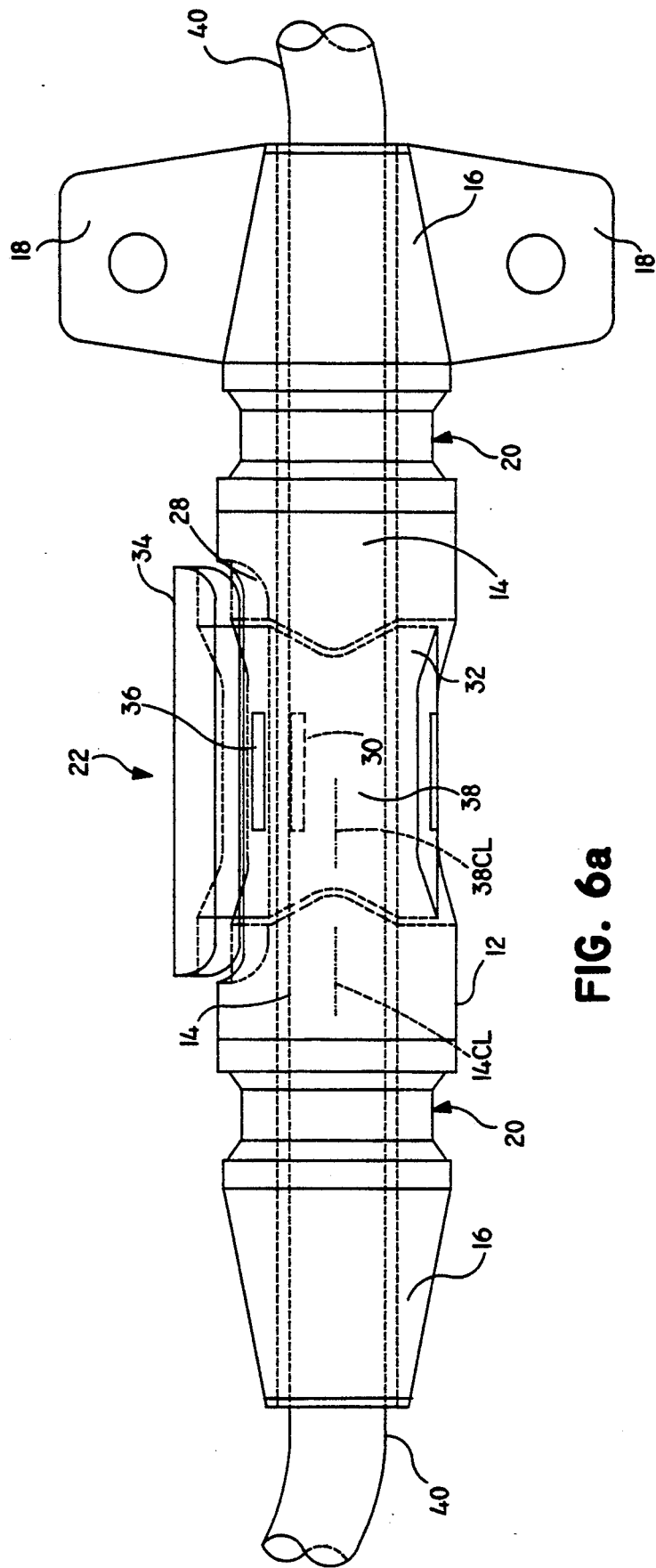
FIGS. 6a and 6b are side views of the sleeve of FIG. 1 having a lead body passing therethrough, with the locking mechanism in unlocked and locked positions, respectively.
Figure 6B:
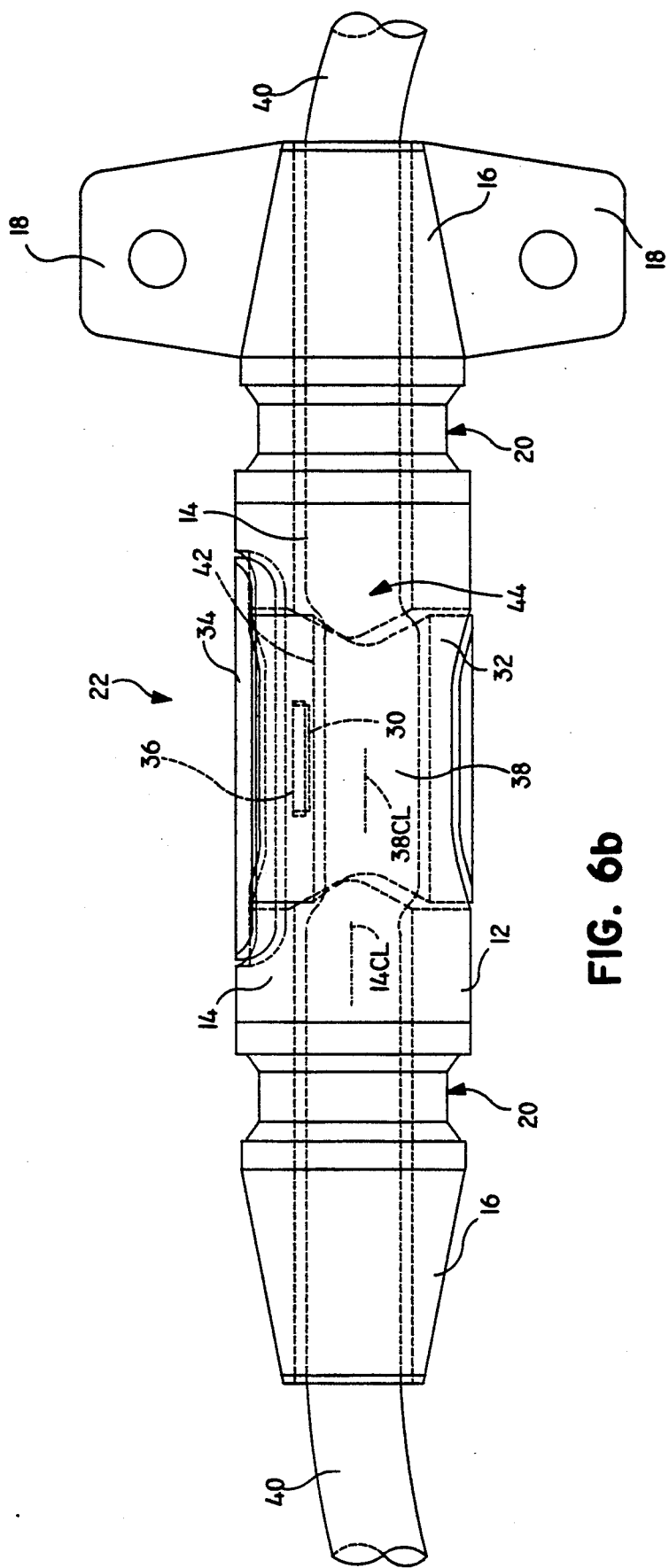

The manner in which the above-described offset of alignment between cylindrical bores 14 and 38 functions to secure sleeve 10 to a lead will perhaps be best understood with reference to FIGS. 6a and 6b. In FIG. 6a, a lead body 40 is shown running axially through the center of sleeve 10; pushbutton 22 is in the first position, previously described with reference to FIG. 5a, in which pushbutton top 34 is raised with respect to the outer surface of sleeve body 12, and cylindrical bores 14 and 38 are in substantial alignment. It is to be noted from FIG. 6a that lead body 40 has a diameter which is only slightly smaller than the common diameter of respective cylindrical bores 14 and 38. Since different types of leads have different diameters, it is contemplated by the inventor that sleeve 10 in accordance with the present invention must be made in different sizes to accommodate different sizes of leads. It is believed that a person having the benefit of this disclosure would be readily able to practice the present invention with any size of lead.

The alignment of cylindrical bores 14 and 38 when locking mechanism is in the position shown in FIG. 6a can be appreciated by comparing the center line (axis) 14CL of cylindrical bore 14 in FIG. 6a with the center line (axis) 38CL of cylindrical bore 38. In the "unlocked" position depicted in FIG. 6a, sleeve 10 is allowed to freely slide back and forth along lead body 40.

In FIG. 6b, pushbutton 22 has been pushed downward into a "locked" position, so that pushbutton top 34 is disposed entirely within shallow recess 28 in sleeve body 12 and is substantially flush with the outer surface of sleeve body 12. Also, in the locked position of FIG. 6b, cylindrical bore 38 is offset slightly from cylindrical bore 14, thus tending to prevent sleeve 10 from sliding along lead body 40. The offset between cylindrical bores 14 and 38 can be appreciated by comparing the center line (axis) 14CL of cylindrical bore 14 in FIG. 6b with the center line (axis) 38CL of cylindrical bore 38.

In the locked position of FIG. 6b, the upper surface 42 of cylindrical bore 38 in plunger 32 is pressed against the upper surface of lead body 40, slightly deflecting lead body 40 generally in the region of oblong channel 26 and plunger 32 within sleeve body 12. This deflection, which occurs at the points designated generally as 44 in FIG. 6b, tends to create significantly increased resistance to back and forth movement of sleeve 10 along lead body 40.

It will be appreciated with reference to FIG. 6b that sleeve 10 does not allow excessive force to be applied to lead body 40. This is because in the locked position of FIG. 6b, pushbutton 22 is prevented from being pushed in further when pushbutton top 32 comes to rest within shallow recess 28 in sleeve body 12. The tightness of the locking action of sleeve 10 onto lead 40 is controlled by the amount of offset between cylindrical bores 14 and 38 when sleeve 10 is locked, and not by the amount of force applied to pushbutton 22.

Figure 7:
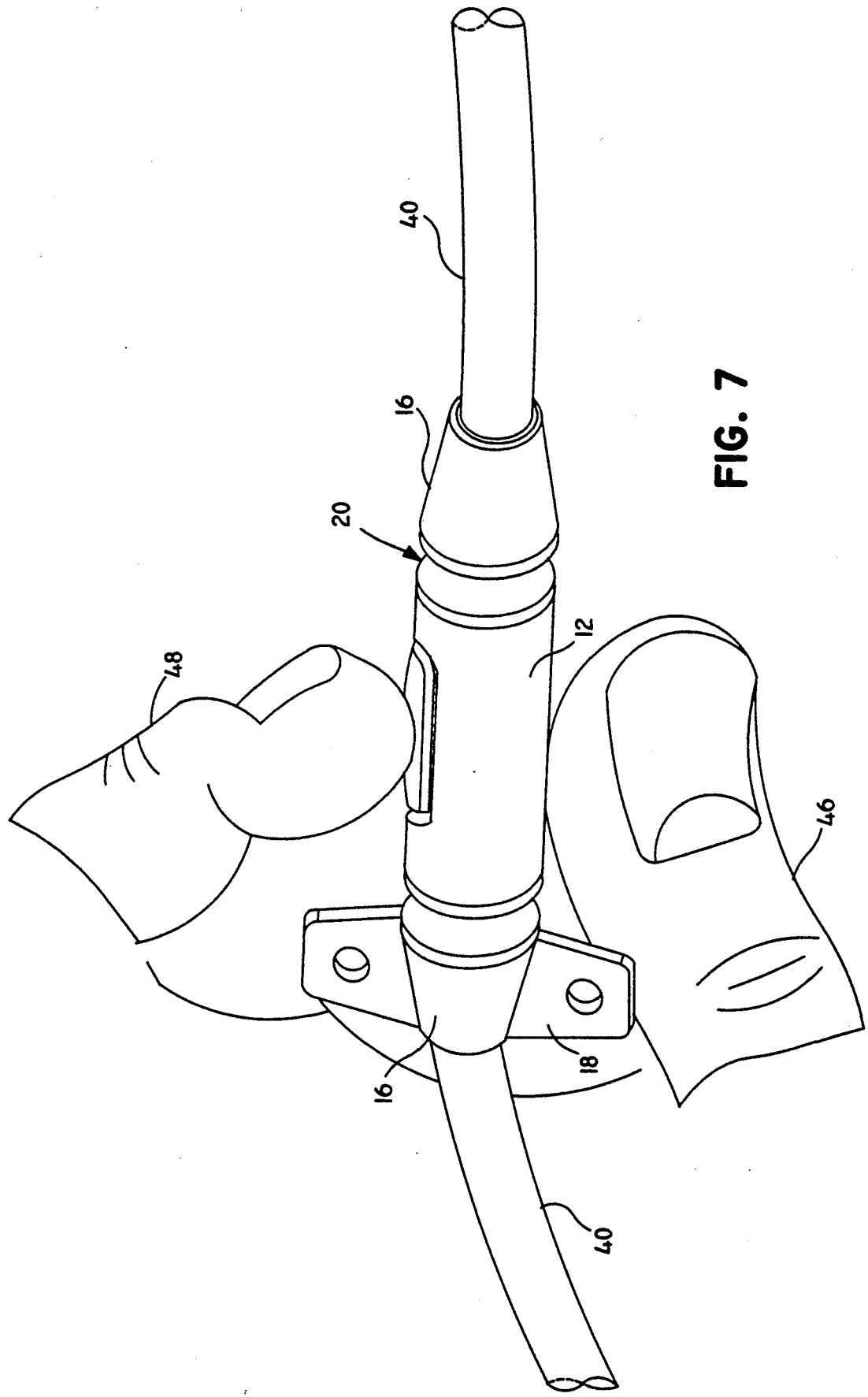
FIG. 7 is an illustration of how the pushbutton locking mechanism of the sleeve of FIG. 1 is actuated.

Pushbutton 22 is depressed into the locked position by squeezing sleeve 10 between the thumb 46 and forefinger 48 as depicted in FIG. 7. When it is depressed into the locked position depicted in FIG. 6b, pushbutton 22 tends to be held in that locked position through the action of longitudinal detents 36 on opposite sides of plunger 32 coming into alignment with corresponding longitudinal indentations 30 in opposite side walls of oblong channel 26. In the unlocked position depicted in FIG. 6a, plunger 32 is compressed slightly so that detents 30 are pressed tightly against the side walls of oblong channel 26. This compression is permitted by virtue of the less than absolute rigidity of both plunger 22 and sleeve body 12. When pushbutton 22 is depressed from the unlocked position (FIG. 6a) to the locked position (FIG. 6b), detents 36 slide downward and into alignment with indentations 30 in sleeve body 12, and decompress or "snap" into place therein. In this way, sleeve 10 is effectively locked into place on lead body 40.

It should be noted that, in accordance with another aspect of the present invention, after sleeve 10 has been locked into a desired position on lead body 40 as depicted in FIGS. 6b and 7, sleeve 10 may be unlocked if necessary by pushing upward on the bottom of plunger 32. Thus, sleeve 10 may be repeatedly locked, unlocked, and repositioned, without difficulty and without risk of damage to the lead.

The inventor has contemplated a number of design options which are available in the practice of the present invention. For example, it is contemplated that pushbutton 22 might be marked (as with a colored dot or other symbol) in order to assist in differentiating between the top and bottom thereof. Also, it is contemplated that some portion of sleeve 10 may have identifying markings to distinguish, for example, between atrial and ventricular leads, or to identify the size, type or other characteristic of the lead.

Figure 8:
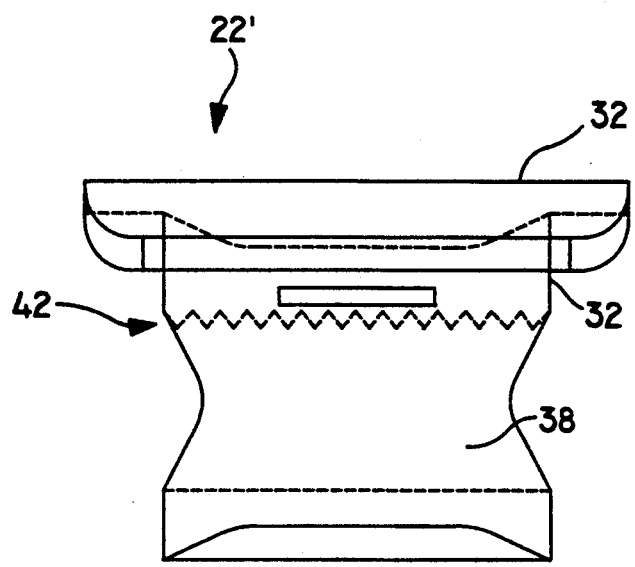
FIG. 8 is a side view of an alternative pushbutton design for the sleeve of FIG. 1.

In the foregoing discussion with reference to FIG. 6b, it was noted that upper surface 42 of cylindrical bore 38 is pressed into contact with lead body 40 when locking mechanism 22 is in the locked position, and that this contact contributes to the locking of sleeve 10 in place. As depicted in FIG. 8, one option contemplated by the inventor is to provide a modified pushbutton 22' having a plurality of ridges 50, or some other texture, on upper surface 42 of cylindrical bore 38, in order to enhance the grip of sleeve 10 onto lead body 40.

Figure 9:
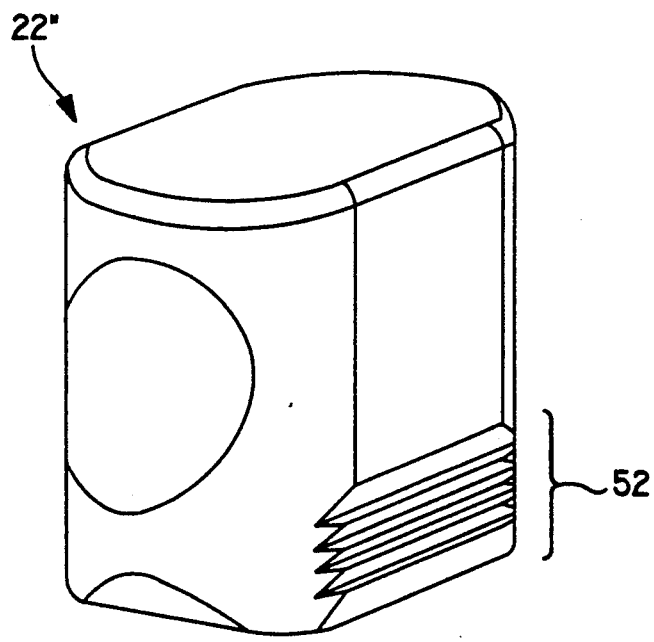
FIG. 9 is a perspective view of another alternative pushbutton design for the sleeve of FIG. 1.

Another option contemplated by the inventor is to provide a modified pushbutton 22" as shown in FIG. 9, having a plurality of ridges 52 on its sides either in addition to or in place of detents 36 previously described with reference to FIG. 4b. Similar, conforming ridges (not shown) could be provided on the sides of oblong channel 26 in sleeve body 12. Ridges 52 would then engage ridges in oblong channel 26, thereby functioning to increase the amount of force required to lock and unlock sleeve 10. In this way, ridges 52 would serve to reduce the possibility of sleeve 10 becoming accidentally unsecured from lead body 40.

Figure 10:
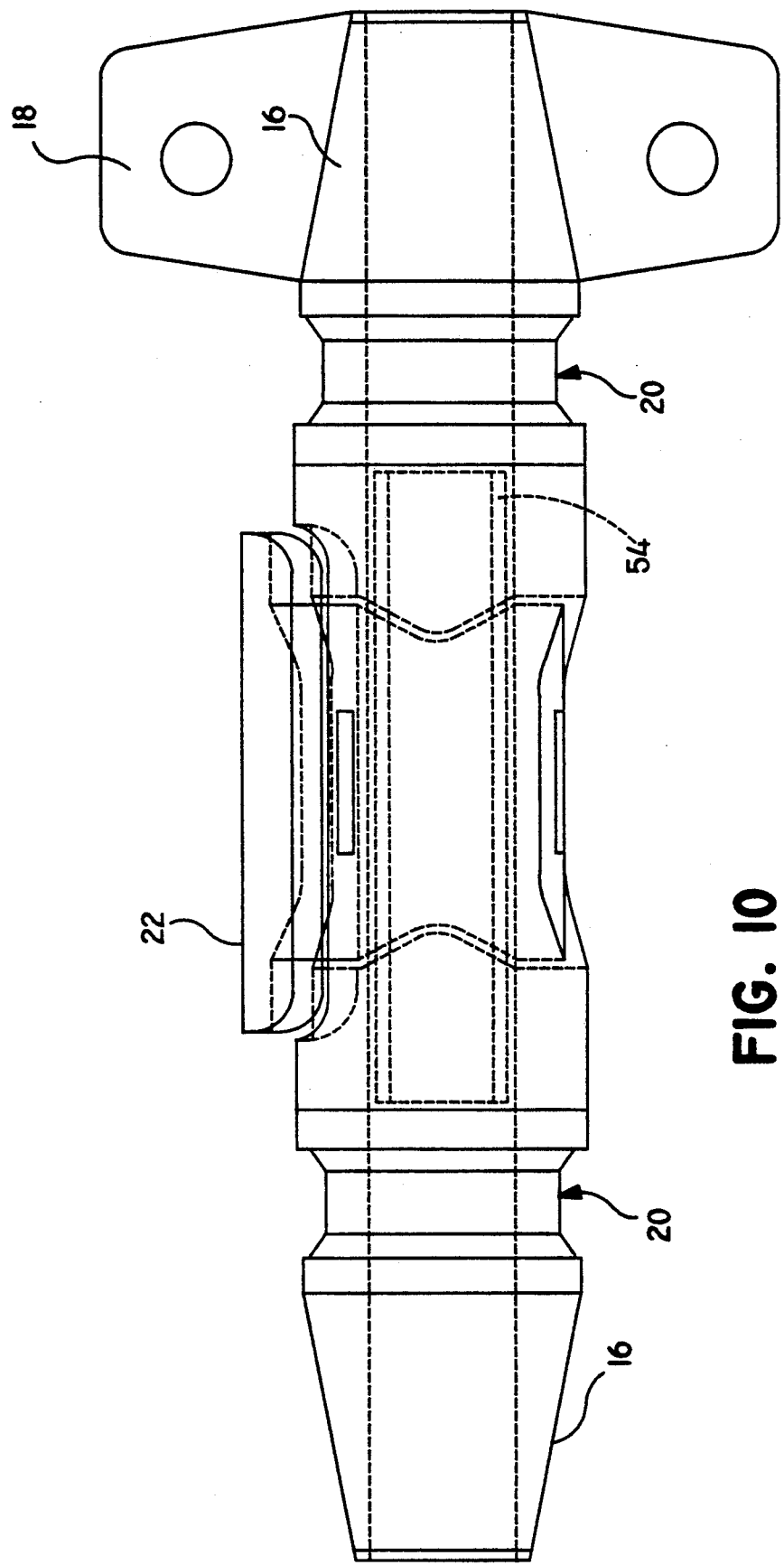
FIG. 10 is a perspective view of an alternative sleeve body design for the sleeve of FIG. 1.

Still another design option available when practicing the present invention would be to utilize pushbutton 22 and a modified sleeve body 12' such as is depicted in FIG. 10. In FIG. 10, a flexible tubular lining 54 is disposed in the cylindrical channel defined by cylindrical bores 14 and 38. A lead, not shown, would pass through the cylindrical channel of the sleeve, the lead also passing through tubular lining 54. Tubular lining 54, which would deflect along with the lead when pushbutton 22 was pushed into a locked position, and would protect the lead from direct contact with pushbutton 22.

From the foregoing detailed description of a specific embodiment of the present invention, it should be apparent that a suture sleeve with a locking mechanism for securing the sleeve to a tubular or cylindrical structure such as an implantable lead has been disclosed. Although a specific embodiment of the invention has been described herein in some detail, it is to be understood that this has been done for the purposes of illustration only, and not for the purpose of limiting the scope of the invention as defined in the following claims. It is contemplated by the inventor that various alterations, substitutions, and modifications (including, but not limited to, those alternatives expressly noted in the foregoing description) may be made to the disclosed embodiment without departing from the spirit and scope of the invention as defined in the claims.

What is claimed is:

1. A suture sleeve adapted to secure a flexible, elongated structure to a patient's body tissue, comprising:
   a sleeve body having a longitudinal throughbore to receive an elongated structure and having a perpendicular channel intersecting said longitudinal throughbore;
   a pushbutton lock member movable within said perpendicular channel and having a throughbore dimensioned to receive said elongated structure;
   said pushbutton lock member upon being depressed moving axially from a first position wherein its throughbore is in substantial coaxial alignment with said sleeve body longitudinal through bore, to a second position offsetting its throughbore with respect to said sleeve body longitudinal throughbore so as to apply pressure against a side portion of said elongated structure extending within said sleeve body longitudinal throughbore to substantially increase frictional resistance against movement of the elongated structure relative to the sleeve body.

2. A suture sleeve in accordance with claim 1, further comprising:
   a first and second collar pieces, each piece having a throughbore dimensioned to receive said elongated structure and affixed to one end of said sleeve body with the collar piece throughbore in substantial coaxial alignment with said sleeve body longitudinal throughbore,
   each of said collar pieces being made of a resilient material and being of a length dimension sufficient to reduce substantial bending of the elongated body in a region of the sleeve body.

3. A suture sleeve in accordance with claim 2, wherein one of said first and second collar pieces has a suture receiving groove formed therein.

4. A suture sleeve in accordance with claim 1, wherein one of said first and second collar pieces further comprises a suture tab projecting therefrom.

5. A suture sleeve in accordance with claim 1, wherein said pushbutton lock member throughbore has textured side walls for enhancing said frictional resistance against movement of said elongated structure through said suture sleeve when said pushbutton lock member is in said second position.

6. A suture sleeve in accordance with claim 1, further comprising:
   at least one longitudinal detent disposed on at least one side of said pushbutton lock member; and
   at least one longitudinal groove formed in at least one side of said perpendicular channel, said at least one groove being adapted to receive said at least one detent when said pushbutton lock member is in said second position, such that said pushbutton lock member is held in said second position.

7. A suture sleeve in accordance with claim 1, wherein a top portion of said pushbutton lock member is flared, and wherein said suture sleeve further comprises a shallow recess formed in said sleeve body, adapted to receive said flared top portion of said pushbutton lock member when said pushbutton lock member is in said second position, and further adapted to prohibit movement of said pushbutton lock member in one direction when said pushbutton lock member is in said second position.

8. A suture sleeve in accordance with claim 7, wherein said flared top portion of said pushbutton lock member is flush with an outer surface of said sleeve body when said pushbutton lock member is in said second position.

* * * * *